United States Patent [19]

Scholl et al.

[11] Patent Number: 4,792,609

[45] Date of Patent: Dec. 20, 1988

[54] INDOLINE AND 1,2,3,4-TETRAHYDROQUINOLINE N(DICARBOALKOXYVINYL) SUBSTITUTED DERIVATIVES

[75] Inventors: Thomas Scholl, Krefeld; Otto Exner, Monheim; Peter Finkel, Cologne; Hermann Perrey, Krefeld, all of Fed. Rep. of Germany

[73] Assignee: Bayer Aktiengesellschaft, Leverkusen, Fed. Rep. of Germany

[21] Appl. No.: 866,039

[22] Filed: May 21, 1986

[30] Foreign Application Priority Data

Jun. 4, 1985 [DE] Fed. Rep. of Germany ....... 3519926

[51] Int. Cl.$^4$ ................ C07D 209/10; C07D 215/06
[52] U.S. Cl. .................................... 546/165; 548/491
[58] Field of Search ....................... 546/165; 548/491

[56] References Cited

U.S. PATENT DOCUMENTS 3,079,366 2/1963 Boyle et al. ........................ 260/45.9

FOREIGN PATENT DOCUMENTS 1568341 3/1970 Fed. Rep. of Germany .
3018132 11/1981 Fed. Rep. of Germany .
0055371 5/1971 Japan ................................... 546/165
1186777 4/1970 United Kingdom ................ 548/491

Primary Examiner—Richard L. Raymond
Assistant Examiner—D. B. Springer
Attorney, Agent, or Firm—Sprung Horn Kramer & Woods

[57] ABSTRACT

An indoline derivative of the formula (I)

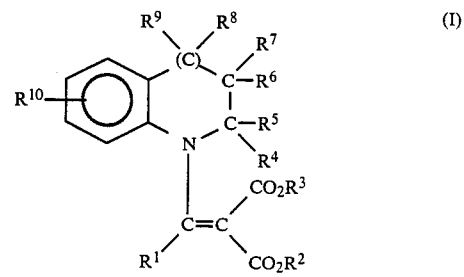

in which $R^1$ denotes H or $C_1$-$C_8$-alkyl;

$R^2$ and $R^3$ are identical or different and denote $C_1$-$C_8$-alkyl;

$R^4$-$R^9$ are identical or different and denote H, $C_1$-$C_8$-alkyl, $C_5$-$C_6$-cycloalkyl or phenyl-$C_1$-$C_4$-alkyl, or $R^5$ and $R^6$ connected together to form a further $C_5$-$C_6$ ring, and $R^{10}$ denotes H or one or more radicals selected from the group consisting of $C_1$-$C_8$-alkyl, $C_1$-$C_8$ alkoxy, $C_5$-$C_6$-cycloalkyl, phenyl-$C_1$-$C_4$-alkyl and carb-$C_1$-$C_8$-alkoxy radicals, or halogen atoms. Such indoline derivative is useful as a UV absorber.

4 Claims, No Drawings

INDOLINE AND 1,2,3,4-TETRAHYDROQUINOLINE N(DICARBOALKOXYVINYL) SUBSTITUTED DERIVATIVES

BACKGROUND OF THE INVENTION

The present invention relates to new indoline derivatives which are suitable as UV absorbers, and to compositions which contain these UV absorbers to protect the skin from UV radiation.

The sun's radiation comprises, inter alia, the range of ultraviolet radiation which can be divided up into various ranges in respect of the action on the human skin:

(a) UV radiation of the wavelength range 285–320 nm (UVB range) causes sunburn (erythema) on people with normal skins, and this is followed by pigmentation based on photoinduced melanogenesis (indirect pigmentation).

(b) UV radiation of the wavelength range 320–400 nm (UVA range) brings about rapid, but weakly developed browning (direct pigmentation). This pigmentation is based on photooxidation of certain precursors of melamine which are present in the skin.

The conventional sunscreen agents contain UVB absorbers which absorb UVB radiation to a greater or lesser extent. However, for particularly light-sensitive people and in order to restrict the total exposure of the skin to UV radiation to a healthy level when the sun's radiation is more intense, there is a need for sunscreen agents which also contain substances absorbing UVA radiation (UVA absorbers).

Beyond the use in cosmetic sunscreen agents, UVA filters are of interest in dermatology for those products which can be used for the chemotherapy of chronic damage due to light, of psoriasis, and of occupational photodermatoses as may occur on dealing with tar, coal and pitch.

Furthermore, there are associations between the exposure of the skin to UVA radiation and its ageing. In addition, it is regarded as being certain that extensive exposure of the skin to UVA radiation signifies, especially when there is a genetically-based sensitivity, a greater risk of suffering from skin cancer. For these reasons, UVA absorbers are of particular significance for cosmetic and medical purposes.

The main requirements of such cosmetic UV absorbers are not their extreme stability to UV and heat as with UV absorbers for plastics, but, in particular:

1. a high specific extinction $E^1$ (which means: economy, less exposure to the formulation and a lower toxicological risk, since less is applied to the skin),
2. excellent oil-solubility (no separation out at low temperatures, for example, during transport or use during winter sports),
3. pH stability
4. toxicological acceptability, and
5. absence of pronounced intrinsic coloration.

It is a fact that, in principle, UVA absorbers for cosmetic purposes are not new. However, the known UVA absorbers do not adequately meet the conditions mentioned above, especially not with regard to the absorption maximum, the level of the specific extinction $E^1$, and the oil-solubility.

SUMMARY OF THE INVENTION

The invention relates to new indoline derivatives which are suitable as cosmetic UV absorbers and which meet the said requirements in an ideal manner. They are represented by formula I below:

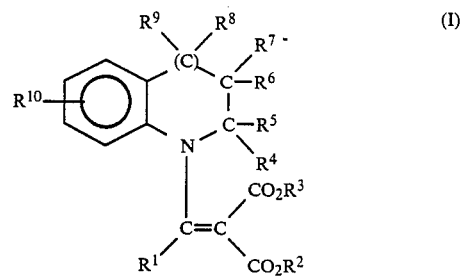

In formula I,
$R^1$ denotes H or $C_1$–$C_8$-alkyl;
$R^2$ and $R^3$ are identical or different and denote $C_1$–$C_8$-alkyl;
$R^4$–$R^9$ are identical or different and denote H, $C_1$–$C_8$-alkyl, $C_5$–$C_6$-cycloalkyl or phenyl-$C_1$–$C_4$-alkyl, it being possible for $R^5$ and $R^6$ to be connected together in such a manner that a further $C_5$–$C_6$ ring is formed, and
$R^{10}$ denotes H or one or more $C_1$–$C_8$-alkyl, $C_1$–$C_8$-alkoxy, $C_5$–$C_6$-cycloalkyl, phenyl-$C_1$–$C_4$-alkyl or carb-$C_1$–$C_8$-alkoxy radicals, or halogen atoms.

The new compounds differ from the known open-chain compounds of the formula II,

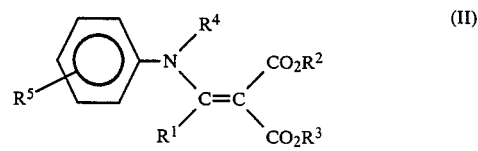

wherein
$R^1$–$R^4$ = H, Alkyl, Aryl
$R^5$ = H, Alkyl, Halogen, Carboxyalkyl, Aryl,
as are described in U.S. Pat. No. 3,079,366, in that they contain the nitrogen as a constituent of a ring fused on to the phenyl nucleus. The result of this difference is that, in a manner which could not have been predicted, the new cyclic compounds of the formula I are considerably more light-fast than the known compounds according to U.S. Pat. No. 3,079,366. However, it is particularly the light-fastness which is of exceptional importance for successful applications as UV absorbers.

Antibacterial skin-care agents IV are disclosed in German Offenlegungsschrift No. 3,018,132, inter alia those of the formula IV a

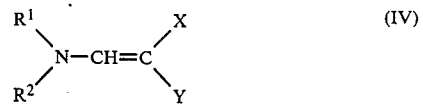

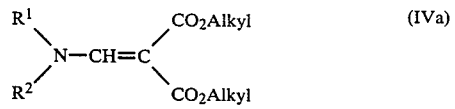

with $R^1$, $R^2$ = H, $C_1$–$C_{14}$-Alkyl, Aryl, Aralkyl, X, Y = $CO_2$Alkyl, CN.

However, the sunscreen action of these compounds and, in particular, the effect of the heterocyclically bonded nitrogen on the position of absorption and the UV stability were not recognized. Another surprising finding of the present invention is the completely opposite pharmaceutical behaviour of aminomethylenemalonic esters and aminomethylenecyanoacetic esters, associated with a position of UVA absorption which may be designated ideal. An additional factor is that the active concentration of the antibacterial skin-care agents according to German Offenlegungsschrift No. 3,018,132 (preferably 3–15%) is significantly above the active concentration of the UVA absorbers according to the invention (preferably 0.1–3%).

Since virtually the entire class of UVA absorbers according to the invention is oily, those skilled in the art will give preference to the compound having the lowest molecular weight, since the absorption/weight ratio is best in this case.

The compounds according to the invention have a high molar extinction coefficient (E), and their absorption maxima are in the range 330–345 nm. Compared with the open-chain compounds of U.S. Pat. No. 3,079,366, the absorption maxima are at markedly longer wavelengths, and it is simply this fact which confers on the compounds of the formula I according to the invention their effectiveness as UVA absorbers. The compounds according to the invention exhibit such a steep decrease towards the visible range that, despite their long wavelength absorption, they have only a very pale yellowish colour.

In contrast to the compounds of German Patent Specification No. 1,568,341, of the general formula III,

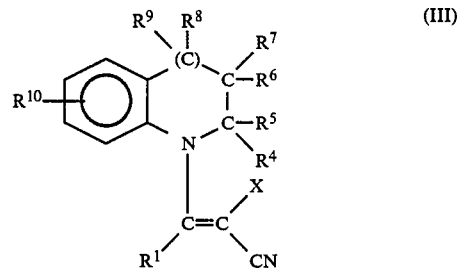

with
X=CN, CO₂alkyl,
R=meaning as in formula I,
all of which are crystalline and sparingly soluble in non-polar solvents, the compounds according to the invention are almost without exception oily and, not least for this reason, are distinguished by having outstanding solubility in all conventional cosmetic formulations.

DETAILED DESCRIPTION OF THE INVENTION

Examples of compounds according to the invention are:

TABLE 1

|   |   | $\lambda_{max}$ | E |
|---|---|---|---|
| 1 | (indoline with HC=C(CO₂C₂H₅)₂) | 330 nm | (32.196) |
| 2 | (2-methylindoline with HC=C(CO₂C₂H₅)₂) | 330 nm | (30.025) |
| 3 | (indoline with H₃C—C=C(CO₂C₂H₅)₂) | 338 nm |   |
| 4 | (2-methylindoline with HC=C(CO₂-iso-C₄H₉)₂) | 331 nm | (26.233) |
| 5 | (2-methylindoline with HC=C(CO₂-n-C₆H₁₃)₂) | 332 nm | (25.310) |
| 6 | (1,2,3,4-tetrahydroquinoline with HC=C(CO₂C₂H₅)₂) | 317 nm | (26.680) |

The UVA absorbers according to the invention can be prepared by processes known per se, for example by reaction of malonic esters (VI) with orthocarboxylic esters (V), such as trimethyl orthoformate, triethyl orthoformate, trimethyl orthoacetate, triethyl orthoacetate, triethyl orthopropionate etc., according to scheme A:

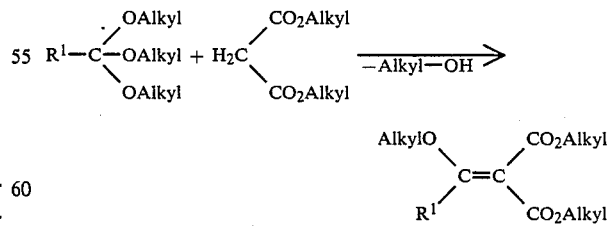

to give the corresponding alkoxyalkylenemalonic esters (VII), followed by condensation, according to scheme B, with NH-heterocycles (VIII), such as indoline, 2-methylindoline, 2,3,3-trimethyl-5-methoxyindoline, 1,2,3,4,10,11-hexahydrocarbazole, 1,2,3,4-tetrahydroquinoline and 1,2,3,4-tetrahydroquinaldine.

Scheme B:

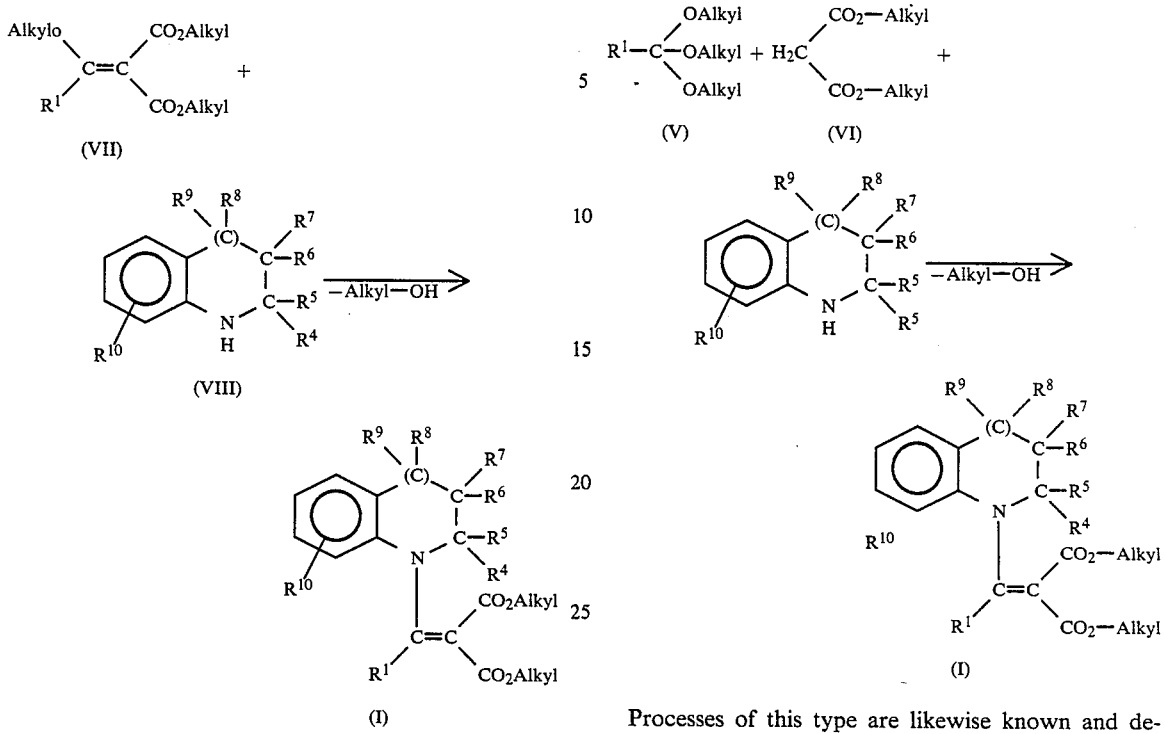

the radicals $R^1$-$R^{10}$ having the meaning mentioned for formula I.

Reactions according to scheme A are known and are described in, for example, *Org. Synthesis Coll.*, Vol. 3, 395 (1955). They are usually carried out in water-removing solvents such as, for example, acetic anhydride and in the presence of catalytic amounts of Lewis acids such as, for example, zinc chloride. Reactions according to scheme B are likewise known and described in, for example, U.S. Pat. No. 3,079,366. They are carried out by heating together the two components at temperatures between 100° C. and 200° C. and removal of the alkanol by distillation.

Another preparation variant comprises the heating together of orthocarboxylic esters, malonic esters and NH-heterocycles, as described in scheme C.

Scheme C:

Processes of this type are likewise known and described in U.S. Pat. No. 3,079,366. The preferred reaction temperatures are between 100° C. and 200° C.

UV absorbers for cosmetic and dermatological sunscreen agents are not new. Thus, for example, sodium 2,2'-dihydroxy-4,4'-dimethoxybenzophenone-5-sulphonate (comparison Example 1), 2,2',4,4'-tetrahydroxybenzophenone (comparison Example 2) and dianisoylmethane (comparison Example 3) are available on the market. The properties of these known compounds are compared with those of the UVA absorbers of the formula I according to the invention in Table 2.

This comparison clearly shows the superior properties of the compounds according to the invention. The known compounds are unsuitable in terms of solubility. Comparison Examples (1) and (2) have a markedly lower specific extinction. In contrast, although comparison Example 3 has a high specific extinction it is at too high a wavelength, so that the important range 320-340 nm is not completely covered.

The invention also relates to sunscreen agents which contain, in an oily phase, at least one of the compounds of the formula I according to the invention as a UVA absorber to protect the skin from UVA radiation, in addition to other suitable cosmetic or dermatological additives.

TABLE 2

| | | specific | solubility at RT | |
|---|---|---|---|---|
| | $\lambda_{max}$ (nm) | extinction $E^1$ | groundnut oil | groundnut/paraffin oil = 1:9 |
| (1) | 330 | 1114 | ∞ | ∞ |

TABLE 2-continued

| | | $\lambda_{max}$ (nm) | specific extinction $E^1$ | solubility at RT groundnut oil | groundnut/paraffin oil = 1:9 |
|---|---|---|---|---|---|
| (2) | [indoline with CH3 at 2-position, N-substituted with HC=C(CO2C2H5)2] | 330 | 1008 | ∞ | ∞ |
| (3) | [indoline, N-substituted with H3C-C=C(CO2C2H5)2] | 338 | | ∞ | ∞ |
| (4) | [2-methylindoline, N-substituted with HC=C(CO2-iso C4H9)2] | 331 | 730 | ∞ | ∞ |
| (5) | [2-methylindoline, N-substituted with HC=C(CO2C6H13)2] | 332 | 582 | ∞ | ∞ |
| (6) | [1,2,3,4-tetrahydroquinoline, N-substituted with HC=C(CO2C2H5)2] | 317 | 878 | ∞ | ∞ |
| Comparison example 1 | | 330 | 160 | — | — |
| Comparison example 2 | | 351 | 645 | 0.8% | — |
| Comparison example 3 | | 362 | 1270 | 1% | — |

These sunscreen agents can be used, for example, for protection from the natural radiation of the sun, for example, when staying in sunlight during recreation or for occupational reasons, from artificial light sources, for example sunray lamp and solarium, and for the treatment of pathogenic sensitivities, for example genetic or occupational, to UVA radiation.

The following oil-soluble UVA filters are, in particular, outstandingly suitable for the purpose explained:
(1) N-(dicarboethoxyvinyl)indoline
(2) N-(dicarboethyoxyvinyl)-2-methylindoline
(3) N-(α-methyl-β,β-dicarboethoxyvinyl)indoline
(4) N-(dicarbo-iso-butoxyvinyl)-2-methylindoline
(5) N-(dicarbohexyloxyvinyl)-2-methylindoline
(6) N-dicarboethoxyvinyl)-1,2,3,4-tetrahydroquinoline Compound (2) is particularly preferred: N-(dicarboethoxyvinyl)-2-methylindoline.

The sunscreen agents according to the invention can be in the form of a liquid which consists of a single phase and which contains a single solvent or a mixture of solvents, for example an oleo-alcohol mixture. They can also be in the form of a dispersion, as a homogeneous paste, as a semisolid product or as a product which contains a propellant. They can form sunscreen agents such as oils, lotions, aerosols (of the oil, foam or spray type) as well as creams for normal or dry skin, milk, lipsticks or any other customary cosmetic or dermatological formulation.

Constituents which may be mentioned for the agents according to the invention, which are defined in detail above, are, in particular, lanolin, vaseline, triglycerides of fatty acids, polyethylene glycols, ethoxylated fatty alcohols, esters such as isopropyl palmitate, isopropyl myristate, isopropyl stearate, oleyl oleate and butyl stearate, animal, vegetable, synthetic or mineral oils, fatty alcohols, lower alcohols, organic and mineral waxes. These constituents are used in amounts of about 1–97% by weight. The compounds of the formula I according to the invention are used in the sunscreen agents according to the invention in a concentration of 0.1 to 10% preferably 0.2 to 10% by weight relative to the weight of the formulation, and especially preferably 0.5 to 6%. The remainder of the formulation being made up to 100% by weight with, on the one hand, customary cosmetic or dermatological ingredients and, on the other hand, the solvent or a mixture of solvents.

Cosmetic and dermatological additives which may be mentioned are thickening agents, soothing and anti-inflammatory agents, superfatting agents, emollients, wetting agents, surface-active agents and preservatives, foam suppressants, perfumes or fragrances or any other utilizable additive as is customary in cosmetics or dermatology for the intended purpose.

The agents according to the invention can be colorless or colored with those colorants and/or pigments which are customarily used for sunscreen agents and, in particular, with iron oxides in proportions from about 0.001 to 0.050% by weight relative to the total weight of the formulation.

If the agent according to the invention contains a propellant, then the propellants based on chlorofluoromethanes are particularly used.

The formulations according to the invention can, in addition to the UVA filters of the formula I, also contain UVB filters such as, for example:
hexyl p-dimethylaminobenzoate,
homomenthyl salicylate,
methyl anthranilate,
isoamyl p-methoxycinnamate,
ethyl α-cyano-β-phenylcinnamate,
2-hydroxy-4-methoxybenzophenone,
3-(4-methylbenzylidene)-D,L-camphor,
2-phenylbenzimidazole-5-sulphonic acid, and
2-phenyl-5-methylbenzoxazole.

The examples mentioned are merely representative of each of the classes of compounds all of which can be used. Further examples are to be found in E. Charlet, P. Finkel, *Ärztliche Kosmetologie* 8, 302–311 (1978). Particularly suitable UVB absorbers are 2-phenyl-5-methylbenzoxazole, 2-phenylbenzimidazole-5-sulphonic acid and isoamyl 4-methoxycinnamate.

EXAMPLE 1

N-(Dicarboethoxyvinyl)-2-methylindoline

A mixture of 216 g of ethoxymethylenemalonic ester and 131 g of 2-methylindone is heated at 150° C. for 5 hours so that 46 g of ethanol is removed by distillation. The residue is then fractionally distilled. About 270 g of yellowish oil of boiling point (0.3) 185° C. are obtained.

EXAMPLES 2-6

The following compounds can be obtained by the process of Example 1:
N-(dicarboethoxyvinyl)indoline, boiling point (0.2) 180° C. (95%)
N-(α-methyl-β,β-dicarboethoxyvinyl)indoline, boiling point (0.3) 178° C.
N-(dicarbo-iso-butoxyvinyl)-2-methylindoline, boiling point (0.4) 195° C. (85%)
N-(dicarbohexyloxyvinyl)-2-methylindoline, boiling point (0.65) 245° C. (80%)
N-(dicarboethoxyvinyl)-1,2,3,4-tetrahydroquinoline, boiling point (0.3) 184° C. (95%).

EXAMPLE 7

Sunscreen Oil

| | |
|---|---|
| N—(Dicarboethoxyvinyl)-2-methylindoline | 3% |
| paraffin oil | 37% |
| isopropyl palmitate | 60% |
| perfume oil | q.s. |

EXAMPLE 8

Sunscreen Oil

| | |
|---|---|
| N—(Dicarboethoxyvinyl)-2-methylindoline | 2% |
| isoamyl p-methoxycinnamate | 2% |
| groundnut oil | 46% |
| paraffin oil | 50% |
| perfume oil | q.s. |

The sunscreen oils are prepared by mixing the listed components.

EXAMPLE 9

Lipsticks

| | |
|---|---|
| Commercially available lipstick base | 94% |
| N—(Dicarboethoxyvinyl)-2-methylindoline | 3% |
| isoamyl p-methoxycinnamate | 3% |

The lipstick base is melted and mixed with the two other components. The composition is poured into cooled molds and, after cooling, the molded articles are removed.

EXAMPLE 10

Sunscreen Spray

| | |
|---|---|
| Mixture of Example 7 | 40% |
| propellant gas mixture of trifluorochloromethane and dichlorofluoromethane 70:50 | 60% |

The two components are introduced into an appropriate compressed gas container.

EXAMPLE 11

O/W Type Sunscreen Cream

| | | |
|---|---|---|
| A | fatty alcohol polyglycol ether based on stearyl-n-cetyl alcohol | 5.0% |
| | duck preen gland fat (artificial) isopropyl palmitate | 6.0% |
| | caprylic/capric acid triglyceride | 11.0% |
| | cetylstearyl alcohol | 2.0% |
| | silicone oil cp 100 | 0.5% |
| | n-(dicarboethoxyvinyl)-2-methylindoline | 2.0% |
| B | water, demineralized | 66% |
| | perfume oil | q.s. |
| | preservative | q.s. |

The components are melted at up to 70° C. and mixed. While stirring, the mixture is added in portions to the water which has been heated to 75° C. The resulting emulsion is slowly cooled to room temperature, continuing the stirring.

EXAMPLE 12

Sunscreen Milk

| | | |
|---|---|---|
| A | Colloidal disperse mixture of cetylstearyl alcohol and sodium cetylstearyl sulphate with a non-ionic emulsifier | 3.15% |
| | decyl oleate | 15.00% |
| | N—(dicarboethoxyvinyl)-2-methylindoline | 2.00% |
| B | water | 79.85% |
| | perfume | q.s. |

Preparation as Example 11.

It will be appreciated that the instant specification and claims are set forth by way of illustration and not limitation, and that various modifications and changes may be made without departing from the spirit and scope of the present invention.

We claim:

1. An indoline derivative of the formula (I)

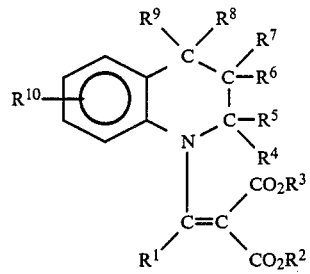

in which
$R^1$ denotes H or $C_1$–$C_8$-alkyl;
$R^2$ and $R^3$ are identical or different and denote $C_1$–$C_8$-alkyl;
$R^4$–$R^9$ are identical or different and dentote H, $C_1$–$C_8$-alkyl, $C_5$–$C_6$-cycloalkyl or phenyl-$C_1$–$C_4$-alkyl, and
$R^{10}$ denotes H or one or more radicals selected from the group consisting of $C_1$–$C_8$-alkyl, $C_1$–$C_8$ alkoxy, $C_5$–$C_6$-cycloalkyl, phenyl-$C_1$–$C_4$-alkyl and carb-$C_1$–$C_8$-alkoxy radicals and halogen atoms.

2. An indoline derivative according to claim 1, wherin the indoline derivative is selected from the group consisting of
N-(dicarboethoxyvinyl)indoline,
N-(dicarboethyoxyvinyl)-2-methylindoline,
N-(α-methyl-β,β-dicarboethoxyvinyl)indoline,
N-(dicarbo-iso-butoxyvinyl)-2-methylindoline and
N-(dicarbohexyloxyvinyl)-2-methylindoline.

3. An indoline derivative according to claim 1, wherein the derivative is N-(dicarboethoxyvinyl)-2-methylindoline.

4. N-(dicarboethoxyvinyl)-1,2,3,4-tetrahydroquinoline.

* * * * *

UNITED STATES PATENT AND TRADEMARK OFFICE
CERTIFICATE OF CORRECTION

PATENT NO. : 4,792,609

DATED : December 20, 1988

INVENTOR(S) : Thomas Scholl, et al

It is certified that error appears in the above-identified patent and that said Letters Patent is hereby corrected as shown below:

| | |
|---|---|
| Title Page, "Foreign Patent Documents", line 3 | Delete "5/1971" and substitute --5/1981-- |
| Col. 9, line 6 | Before "customary" insert --the-- |
| Col. 10, line 52 | Delete "5.0%" |
| Col. 10, line 55 | Delete "6.0%" and substitute --5.0%-- |
| Col. 10, line 56 | After "isopropyl palmitate" insert --6.0%-- |
| Col. 11, line 21 | Insert --preservative     q.s.-- |

Signed and Sealed this

Sixth Day of February, 1990

Attest:

JEFFREY M. SAMUELS

Attesting Officer     Acting Commissioner of Patents and Trademarks